(12) United States Patent
Jung et al.

(10) Patent No.: US 8,221,787 B2
(45) Date of Patent: Jul. 17, 2012

(54) PHARMACEUTICAL PREPARATION FOR ORAL ADMINISTRATION WITH CONTROLLED ACTIVE INGREDIENT RELEASE IN THE SMALL INTESTINE AND METHOD FOR ITS PRODUCTION

(75) Inventors: Gerd Jung, Breitengüssbach (DE); Albert Schaupp, Strullendorf (DE)

(73) Assignee: Dr. Robert Pfleger Chemische Fabrik GmbH, Bamberg (DE)

( * ) Notice: Subject to any disclaimer, the term of this patent is extended or adjusted under 35 U.S.C. 154(b) by 593 days.

(21) Appl. No.: 12/309,198

(22) PCT Filed: Jul. 5, 2007

(86) PCT No.: PCT/EP2007/005970
§ 371 (c)(1),
(2), (4) Date: Jan. 23, 2009

(87) PCT Pub. No.: WO2008/006506
PCT Pub. Date: Jan. 17, 2008

(65) Prior Publication Data
US 2009/0285891 A1  Nov. 19, 2009

(30) Foreign Application Priority Data
Jul. 10, 2006  (EP) .................................... 06014244

(51) Int. Cl.
*A61K 9/20* (2006.01)
*A61K 9/28* (2006.01)
*A61K 9/40* (2006.01)

(52) U.S. Cl. .................... 424/464; 424/474; 424/475

(58) Field of Classification Search ........................ None
See application file for complete search history.

(56) References Cited

U.S. PATENT DOCUMENTS

| 6,780,436 | B1 | 8/2004 | López-Cabrera et al. | |
| 2004/0208925 | A1* | 10/2004 | Oner et al. | 424/465 |
| 2005/0123606 | A1* | 6/2005 | Kidane | 424/464 |
| 2005/0191351 | A1* | 9/2005 | Kidane et al. | 424/468 |
| 2006/0086657 | A1* | 4/2006 | Kools | 210/490 |

FOREIGN PATENT DOCUMENTS

| EP | 0 335 560 A2 | 10/1989 |
| EP | 1 086 694 A2 | 3/2001 |
| WO | WO 98/51287 | 11/1998 |
| WO | WO 01/68058 A1 | 9/2001 |
| WO | WO 01/87269 A1 | 11/2001 |

OTHER PUBLICATIONS

Meis, S., et al., Correlation of Drug Permeation Through Isolated Films and Coated Dosage Forms Based on kollicoat SR 30 D/IR, AAPS Annual Meeting and Exposition (2004), p. 1.*
Baker, Richard W., Membrane Technology and Applications, (2004), pp. 1-14.*
Jinan Jinda Pharmaceutical, Trospium Chloride, (date accessed Sep. 9, 2011), p. 1.*
Pharm-a-spheres, Product specification, (date accessed: Sep. 9, 2011), p. 1.*
Cerea, Matteo, et al., A novel powder coating process for attaining taste masking and moisture protective films applied to tablets, International Journal of Pharmaceutics 279 (2004) pp. 127-139.*

* cited by examiner

*Primary Examiner* — Scott Long
*Assistant Examiner* — Lyndsey Beckhardt
(74) *Attorney, Agent, or Firm* — The Nath Law Group; Tanya E. Harkins

(57) ABSTRACT

Any pharmaceutical preparation for oral administration with controlled release of active ingredient in the small bowel, on the basis of active ingredient carriers provided with at least one active ingredient which are provided with an inner layer to control the release of active ingredient and with a gastro-resistant coating layer disposed thereon, which is characterized in that the inner layer is formed from at least two diffusion layers whose permeability for the diffusing active ingredient decreases from the inside to the outside, and a method for the production thereof, are described.

1 Claim, 1 Drawing Sheet

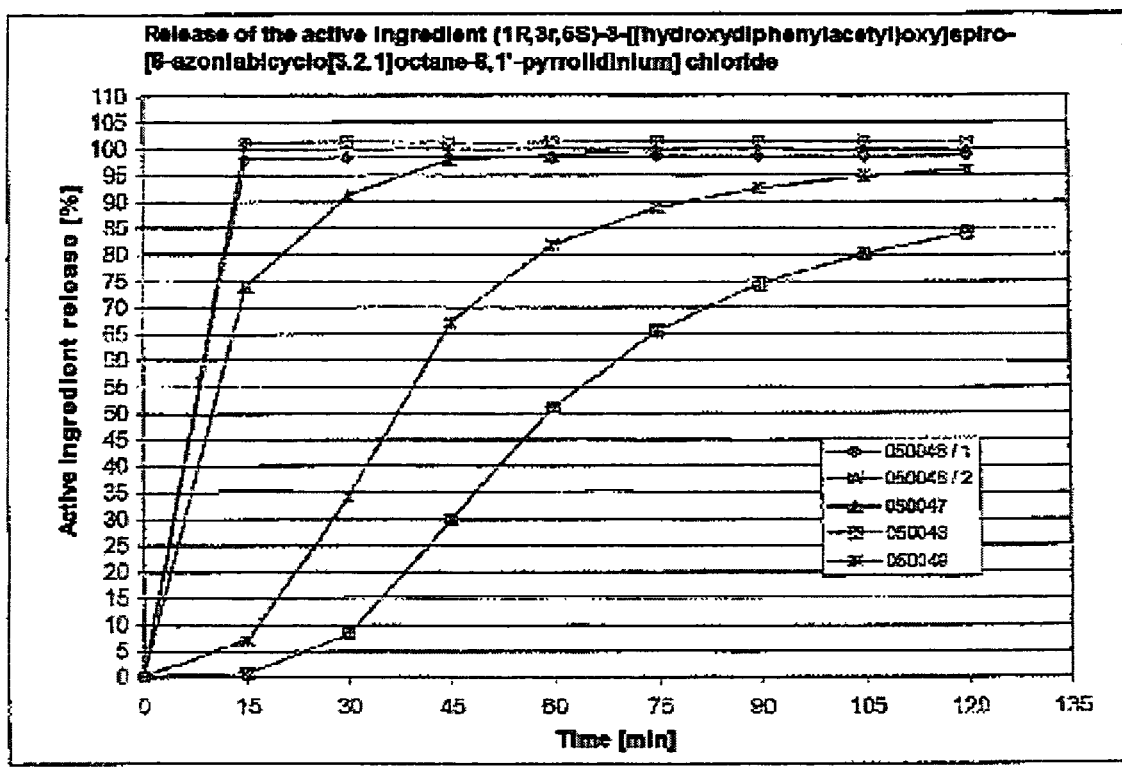

PHARMACEUTICAL PREPARATION FOR ORAL ADMINISTRATION WITH CONTROLLED ACTIVE INGREDIENT RELEASE IN THE SMALL INTESTINE AND METHOD FOR ITS PRODUCTION

The present invention relates to a pharmaceutical preparation for oral administration with controlled release of active ingredient in the small bowel on the basis of active ingredient carriers which are provided with at least one active ingredient and which are provided with an inner layer to control the release of active ingredient and with a gastro-resistant coating layer disposed thereon, and a method for the manufacture thereof.

Pharmaceutical preparations for oral administration with controlled release of active ingredient in the small bowel have previously been disclosed.

Thus, DE 198 23 940 A1 describes enteric fluoxetine pellets which include a neutral core onto which a fluoxetine layer has been applied and which is followed by a separating layer onto which an enteric layer is applied and is optionally provided with a finishing layer. In this case, the enteric layer serves to ensure that the active ingredient passes through the patient's stomach unchanged and dissolves only when the active ingredient leaves the stomach and enters the small bowel.

EP 0 941 070 B1 relates to a suckable tablet for modified release of active ingredients in the gastrointestinal tract, which comprises an active ingredient preparation in the form of particles with an at least bilayer coating, where an outer coating layer is saliva-resistant but gastro-soluble, and an inner coating layer is substantially resistant to disintegration in aqueous media but permits sustained release of active ingredient by diffusion. In a further embodiment, the particles with a bilayer coating include an outer coating layer which is saliva-resistant but gastro-soluble, and an inner coating layer which is gastro-resistant but soluble in the small bowel.

US patent application US 2004/0142035 A1 discloses a pharmaceutical preparation which has a core which comprises one or more active pharmaceutical ingredients, and a coating layer enveloping the core, where the coating layer includes a combination of two or more enteric coating materials, of which at least two of the enteric coating materials dissolve at different pH values, in order in this way to achieve a controlled release profile of the active ingredient depending on the pH. This design serves to prevent a significant part of the active ingredient still being present in the product after passing through the small bowel, and being lost.

Conventional pharmaceutical preparations for oral administration with controlled release of active ingredient in the small bowel have, however, not proved to be entirely satisfactory because, when the active ingredient is released in the small bowel, there is initially a large rise in the active ingredient release with correspondingly high blood levels, leading in many cases to an increase in the rate and intensity of side effects. With substances mentioned hereinafter, this relates for example in particular to dry mouth, accommodation impairments, gastrointestinal problems or central nervous effects. This is particularly disadvantageous when the entire dose of the active ingredient is to be administered only once a day. It is further observed that oral administration for example of anticholinergics is followed by a large inter-individual variation in the plasma profiles.

On the other hand, the use of enteric materials with different solubilities at different pH values, as envisaged by the teaching of US 2004/0142035 A1, results in limitations on the choice of materials on the one hand, and on the other hand non-uniform release of active ingredient when there are pH fluctuations.

The object of the present invention is therefore to provide a pharmaceutical preparation of the type indicated at the outset for oral administration of active ingredients with controlled release active ingredient in the small bowel, which, in contrast to conventional formulations, exhibits a smaller initial rise in the release of active ingredient, and thus a lower initial plasma peak of the active ingredient, but ensures subsequently a lower but uniform plasma concentration of the active ingredient, and thus leads to a lower rate of side effects and intensity of side effects and to a smaller interindividual variation of the plasma profiles, especially when the entire dose of the active ingredient is to be administered only once a day.

This is achieved with the provided preparation when the release rate of the active ingredient is <75% in 60 minutes on in vitro testing of the release in accordance with the US Pharmacopeia. It is thus possible without problems to ensure the necessary dose for the whole day with a single administration.

It has surprisingly emerged that this object can be achieved by providing the active ingredient carrier-provided with an active ingredient with an inner layer to control the release of active ingredient, which is formed from at least two diffusion layers whose permeability for the diffusing active ingredient decreases from the inside to the outside and which are further provided with a gastro-resistant coating layer disposed thereon.

The invention therefore relates to the pharmaceutical preparation according to the main claim and the use thereof.

The invention thus relates to a pharmaceutical preparation for oral administration with controlled release of active ingredient in the small bowel, on the basis of active ingredient carriers provided with at least one active ingredient which are provided with an inner layer to control the release of active ingredient and with a gastro-resistant coating layer disposed thereon, which is characterized in that the inner layer is formed from at least two diffusion layers whose permeability for the diffusing active ingredient decreases from the inside to the outside.

This formation of the inner layer comprising at least two diffusion layers makes it possible to bring about targeted release of the active ingredient in the small bowel, so that, compared with conventional products of this type, a lower initial rate of release of active ingredient can be achieved, leading on administration of the entire daily dose of the active ingredient in a single dose, with appropriately low but sufficient blood levels, to a smaller interindividual variation in the plasma profile and thus to a reduced rate and intensity of side effects.

In a preferred embodiment of the invention, the at least two diffusion layers of the inner layer for controlling the release of active ingredient are formed from a matrix material which is insoluble in small bowel fluid and into which pore formers which control the permeability for the diffusing active ingredient and are soluble and/or swellable and/or water-absorbing in small bowel fluid are incorporated. It is possible in this connection for the diffusion layers to comprise matrix materials which are identical or of different types, and/or one or more pore formers which are of identical or different types.

Thus, according to the invention, the permeability of the diffusion layers for the diffusing active ingredient is preferably controlled via the nature, the quantity and/or the particle size and/or the solubility and/or the swellability and/or the water-absorbing capacity of the pore formers present in the matrix material.

According to the invention, the inner layer has an inner and an outer diffusion layer for controlling the release of active ingredient, and in the case where the pore former material and matrix material are identical, the particle size and/or the concentration of the pore formers in the inner diffusion layer is greater than in the outer diffusion layer. In a preferred embodiment, when the pore formers are soluble in small bowel fluid, the ratio of the pore former concentration in the inner diffusion layer to the pore former concentration in the outer diffusion layer is in the range from 20:1 to >1:1, preferably in the range from 10:1 to 1.1:1.

The matrix material of the diffusion layers is preferably selected from the group comprising ethylcellulose, cellulose acetate phthalate, cellulose acetate succinate, shellac, hydroxypropylmethylcellulose acetate succinate, cellulose acetate, cellulose acetate propionate, hydroxypropylmethylcellulose phthalate, polyvinyl acetate, polyvinyl acetate phthalate, cellulose acetate butyrate, butyl methacrylate-(2-dimethylaminoethyl)methacrylate-methyl methacrylate copolymers, ethyl acrylate-methyl methacrylate copolymers, methacrylic acid-methyl methacrylate copolymers, methacrylic acid-ethyl acrylate copolymers, ethyl acrylate-methyl methacrylate-trimethylammoniumethyl methacrylate chloride copolymers, sodium carboxymethylcellulose, methylcellulose, hydroxyethylcellulose, methylethylcellulose, methylhydroxypropylcellulose, hydroxypropylmethylcellulose, hydroxyethylmethylpropylcellulose, chitosan, chitosan acetate, silicone elastomer latex suspensions, hydrogenated castor oil, stearic acid, glycerol monostearate, glycerol distearate, glycerol dibehenate, stearyl alcohol, white wax, yellow wax, hydrogenated vegetable oil and microcrystalline wax.

The material chosen for the pore formers of the diffusion layers comprises materials from the group comprising polyvinyl alcohol-polyethylene glycol copolymers, polyvinylpyrrolidone, vinylpyrrolidone-vinyl acetate copolymers, crosslinked polyvinyl-pyrrolidone, microcrystalline cellulose, hydroxypropyl-cellulose, sodium carboxymethylcellulose, methylcellulose, hydroxyethylcellulose, methylethylcellulose, methylhydroxypropylcellulose, hydroxypropylmethylcellulose, hydroxyethylmethylpropylcellulose, poly-ethylene glycol, cellulose powder, sucrose, lactose, mannitol, sorbitol and polysorbate.

The matrix material of the diffusion layers may if necessary additionally comprise plasticizers and antitack agents in order to adjust the property of the matrix material of the diffusion layers in the desired manner. The matrix material of the diffusion layers preferably provides polyethylene glycol, propylene glycol, triethyl citrate, triacetin, acetyl tributyl citrate, polysorbates, 2-pyrrolidone, dibutyl sebacate, stearic acid, castor oil and/or medium-chain triglycerides as plasticizers, and talc, stearic acid and salts thereof, fatty alcohols, mono-, di- or triglycerides with straight- and/or branched-chain fatty acids, colloidal silicon dioxide, precipitated silicon dioxide, aluminium oxide, kaolin, maize starch, wheat starch, rice starch, potato starch, titanium dioxide, silicone emulsions and/or Veegum (a magnesium aluminium silicate dispersion) as antitack agent.

The active ingredient carriers present in the pharmaceutical preparation of the invention may comprise as active ingredient any active pharmaceutical ingredients whose effect can be ensured via the small bowel, such as, for example, 4-diethylamino-2-butynyl α-phenylcyclohexaneglyconate hydrochloride, ethyl-dimethyl(1-methyl-3,3-diphenylpropyl)ammonium carra-geenate, (+)-[R-2-[α-2-(diisopropylamino) ethyl]benzyl]-p-cresol tartrate, 8-(cyclopropylmethyl)-6β, 7β-epoxy-3α-hydroxy-1αH,5α)-(S)-tropate bromide, (1R, 3r,5S)-3-[(hydroxydiphenylacetyl)oxy]spiro[8-azonia-bicyclo[3.2.1]octane-8,1'-pyrrolidinium]chloride, 2-diethylaminoethyl (bicyclohexyl)-1-carboxylate hydrochloride, 1-methyl-4-piperidyl diphenylpropoxy-acetate hydrochloride, (3R)-1-azabicyclo[2.2.2]oct-3-yl (1S)-1-phenyl-3,4-dihydroisoquinoline-2(1H)-carboxylate succinate, (S)-1-[2-(2,3-dihydro-5-benzofuranyl)ethyl]-α,α-diphenyl-3-pyrrolidineacetamide hydrobromide, (8R)-3α-hydroxy-5-isopropyl-1αH,5αH-tropanium bromide (±tropate), 8-butyl-6β,7β-epoxy-3α-[(S)-3-hydroxy-2-phenylpropanoyloxy] tropanium bromide, (+)-(S)—N-methyl-γ-(1-naphthyloxy)-2-thiophenepropylamine, 2-[(1R)-3-(diisopropylamino)-1-phenylpropyl]-4-(hydro-oxymethyl)phenyl isobutyrate, 4-(diethylamino)-but-2-yn-1-yl (2S)-cyclohexyl(hydroxy) phenylacetate, ethyldi-methyl(1-methyl-3,3-diphenylpropyl)ammonium bromide, 2-piperidinoethyl 3-methyl-4-oxo-2-phenyl-4H-chromene-8-carboxylate hydrochloride, benzyl(2-chloroethyl)-(1-methyl-2-phenoxyethyl)amine hydrochloride and/or a salt or another salt of these active ingredients.

The active ingredient is preferably present in an amount of from 1 to 250 mg per dose unit on the active ingredient carriers, preferably in an amount which corresponds to the daily dose. It is moreover possible for the active ingredient to be present in the form of a coating on the active ingredient carriers, which coating may, besides the active ingredient, optionally additionally comprise a binder and optionally antitack agent and/or buffer substances in order to control the release of the active ingredient in the desired manner.

The active ingredient carriers are preferably in the form of neutral pellets and/or crystalline substances and/or granulated or extruded carrier substances and advantageously have a particle size of from 0.1 to 3.0 mm, preferably from 0.2 to 2.0 mm.

Such active ingredient carriers are commercially available and include as carrier material for example sugar, starch, microcrystalline cellulose, dicalcium phosphate, sodium chloride, citric acid, tartaric acid, malic acid, sucrose, lactose, sorbitol, mannitol, cellulose, calcium hydrogen phosphate, sodium citrate, tricalcium phosphate, maize starch, wheat starch, potato starch, rice starch and/or mixtures thereof.

In an advantageous embodiment of the invention, the active ingredient carriers provided with the active ingredient comprise per dose unit from 1 to 250 mg, advantageously 5 to 100 mg, more preferably 20 to 60 mg of the active ingredient, from 10 to 500 parts by weight of carrier material, from 1 to 100 parts by weight of binder, from 1 to 100 parts by weight of antitack agent and from 1 to 100 parts by weight of buffer substances.

The binder of the active ingredient carrier provided with the active ingredient can be selected from the group comprising hydroxypropylmethylcellulose, butyl methacrylate-(2-dimethylaminoethyl)methacrylate-methyl methacrylate copolymers, ethyl acrylate-methyl methacrylate copolymers, methacrylic acid-methyl methacrylate copolymers, methacrylic acid-ethyl acrylate copolymers, methyl acrylate-methyl methacrylate-methacrylic acid copolymers, ethyl acrylate-methyl methacrylate-trimethylammoniumethyl methacrylate chloride copolymers, ethylcellulose, sodium carboxymethylcellulose, methylcellulose, hydroxyethylcellulose, methylethylcellulose, hydroxyethylmethylpropylcellulose, polyvinylpyrrolidone, polyvinyl acetate, vinylpyrrolidone-vinyl acetate copolymers, polyethylene glycol, gelatin, maize starch, wheat starch, rice starch and potato starch and mixtures thereof.

The active ingredient carrier provided with the active ingredient may comprise as antitack agent talc, stearic acid and salts thereof, mono-, di-, triglycerides with straight- and/or branched-chain fatty acids, fatty alcohols, colloidal silicon dioxide, precipitated silicon dioxide, aluminium oxide, hydrogenated castor oil and macrogol (polyethylene glycol) and mixtures thereof.

Buffer substances which can be employed to prevent possible pH shifts in the bowel region of the active ingredient carriers provided with the active ingredient are sodium hydroxide, citric acid, tartaric acid, phosphoric acid, ascorbic acid, succinic acid, adipic acid, fumaric acid and their pharmaceutically acceptable salts and mixtures thereof.

The gastro-resistant coating layer disposed on the inner layer to control the release of active ingredient is preferably formed from the group comprising ethylcellulose, cellulose acetate phthalate, cellulose acetate succinate, shellac, hydroxypropylmethylcellulose acetate succinate, cellulose acetate, cellulose acetate propionate, hydroxypropylmethylcellulose phthalate, polyvinyl acetate phthalate, cellulose acetate butyrate, butyl methacrylate-2-dimethylaminoethyl methacrylate-methyl methacrylate copolymer, ethyl acrylate-methyl methacrylate copolymer, methacrylic acid-methyl methacrylate copolymer, methacrylic acid-ethyl acrylate copolymer, methacrylic acid-methyl methacrylate copolymer, methyl acrylate-methyl methacrylate-methacrylic acid copolymer, ethyl acrylate-methyl methacrylate-trimethylaminoethyl methacrylate chloride copolymer and/or mixtures thereof.

With one type of intake of the active ingredient carriers, in which the latter come directly into contact with the saliva in the mouth, it is possible, because of the pH conditions, for the gastro-resistant layer to dissolve, in which case active ingredient is released there. In order to prevent this, it is preferred according to the invention to provide the active ingredient carriers, which have been provided with the active ingredient, the diffusion layer and, where appropriate, the gastro-resistant coating, with a saliva-resistant outer layer which is preferably formed from ethylcellulose, cellulose acetate phthalate, cellulose acetate succinate, shellac, hydroxypropylmethylcellulose acetate succinate, cellulose acetate, cellulose acetate proprionate, hydroxypropylmethylcellulose phthalate, polyvinyl acetate, polyvinyl acetate phthalate, polyvinyl alcohol-polyethylene glycol copolymer, cellulose acetate butyrate, butyl methacrylate-2-dimethylaminoethyl methacrylate-methyl methacrylate copolymer, ethyl acrylate-methyl methacrylate copolymer, methacrylic acid-methyl methacrylate copolymer, methacrylic acid-ethyl acrylate copolymer, methacrylic acid-methyl methacrylate copolymer, methyl acrylate-methyl methacrylate-methacrylic acid copolymer, ethyl acrylate-methyl methacrylate-trimethylaminoethyl methylacrylate chloride copolymer and/or mixtures thereof.

The saliva-resistant outer layer can if desired comprise aromatizing substances, flavourings and/or sweeteners.

In a further preferred embodiment of the invention, the active ingredient carriers which have been provided with the active ingredient, the diffusion layers, the gastro-resistant coating layer, and, where appropriate, the saliva-resistant outer layer, are compressed to tablets using conventional excipients, or packed into capsules made of gelatin, cellulose, starch or starch derivatives, or are in the form of liquids or semisolid or solid preparations for preparing a suspension or a suspension gel.

The pharmaceutical preparation of the invention can be produced using procedures known per se, for example by the active ingredient carrier, which is for example in the form of commercially available pellets, being coated with a solution or suspension which comprises the active ingredient, the binder, the antitack agent and, where appropriate, buffer substances, then providing the intermediate product obtained in this way successively with at least two diffusion layers whose permeability for the diffusing active ingredient decreases from the inside to the outside, applying the gastro-resistant coating layer and, where appropriate, providing a saliva-resistant outer layer.

It has emerged that the control according to the invention of the release of active ingredient via the inner layer composed of at least two diffusion layers whose permeability for the diffusing active ingredient decreases from the inside to the outside has the surprising advantage that, by comparison with other known formulations, there is a smaller increase in release of active ingredient and thus the desired lower blood levels of the active ingredient are obtained, with the active ingredient release characteristics surprisingly being even more favourable by comparison with the teaching of US 2004/0142035 A1 through the fact that two layers differing in diffusion permeability are applied instead of one layer which comprises the two materials with different diffusion characteristics in the form of a mixture.

This situation is to be explained in more detail by the following examples and comparative examples.

Two dosage forms are possible and preferred for the pharmaceutical preparation of the invention:
1. A capsule which is filled with the active ingredient carriers provided with the active ingredient, the diffusion layers, the gastro-resistant coating layer and the optional saliva-resistant outer layer;
2. A tablet which has been obtained by compressing the active ingredient carriers provided with the active ingredient, the diffusion layers, the gastro-resistant coating layer and, where appropriate, the saliva-resistant outer layer with use of conventional excipients.

The tablet may be divisible and can either be swallowed with liquid, taken with suitable food in small pieces, or else sucked or allowed to disintegrate in the mouth, without the desired release of active ingredient in the small bowel being impaired thereby, because with these types of intake the tablet disintegrates into the individual or agglomerated active ingredient carriers, which active ingredient carriers each comprise the active ingredient, the diffusion layers and the gastro-resistant coating layer, thus ensuring the desired active ingredient release profile.

The presence of a saliva-resistant outer layer with the types of intake of the pharmaceutical preparation results in no impairment of the gastro-resistant layer because of the pH conditions in the mouth, and thus the active ingredient is not released in the mouth but, as intended, only in the small bowel.

EXAMPLE 1

Batch: 050046/2

Pharmaceutical Preparation of the Invention in the Form of Pellets with an Active Ingredient Content of 45 mg of (1R,3r,5S)-3-[(hydroxydiphenylacetyl)oxy]spiro[8-azoniabicyclo[3.2.1]octane-8,1'-pyrrolidinium]chloride as Active Ingredient Per Dosage Unit The ingredients for producing the active ingredient carriers provided with active ingredient are listed in Table 1 below.

TABLE 1

Formulation, application of the active ingredient

| No. | Starting material | per dose mg |
|---|---|---|
| 1 | Active ingredient* | 45.000 |
| 2 | Neutral pellets | 100.000 |
| 3 | Hydroxypropylmethylcellulose (hypromellose) | 4.500 |
| 4 | Talc | 4.500 |
| 5 | Polyethylene glycol (macrogol 6000) | 0.450 |
| | Total amount per dose | 154.450 |

*(1R,3r,5S)-3-[(Hydroxydiphenylacetyl)oxy]spiro-[8-azoniabicyclo[3.2.1]octane-8,1'-pyrrolidinium]chloride The neutral pellets are sugar-starch pellets with a particle size in the range from 0.1 to 3.0 mm. The active ingredient, the hydroxypropylmethylcellulose and macrogol 6000 are dissolved in water, and talc is suspended in the solution. The suspension is continuously sprayed onto the active ingredient carriers in a fluidized bed granulator, and simultaneously dried at an inlet air temperature of 30° C. to 80° C.

Subsequently, diffusion layer 1 is applied to the active ingredient carriers provided with the active ingredient in this way, using the ingredients indicated in Table 2 below:

TABLE 2

Formulation, application of a diffusion layer for optimized release of active ingredient
Formulation of diffusion layer 1

| No. | Starting material | per dose mg |
|---|---|---|
| 1 | Active ingredient pellets (as in Table 1) | 154.450 |
| 2 | Polyvinyl acetate stabilized with polyvinylpyrrolidone and sodium lauryl sulphate (Kollicoat SR 30 D) | 9.000 |
| 3 | Polyvinyl alcohol-polyethylene glycol copolymer (Kollicoat IR) | 1.8000 |
| 4 | Propylene glycol | 0.900 |
| 5 | Talc | 0.360 |
| | Total amount per dose | 166.510 |

Diffusion layer 1 is produced by spraying the active ingredient carriers which have been provided with the active ingredient and obtained using the ingredients indicated in Table 1 with an aqueous suspension of polyvinyl acetate as matrix material and polyvinyl alcohol-polyethylene glycol copolymer as pore former, propylene glycol as plasticizer and talc as antitack agent.

Subsequently, diffusion layer 2 is applied using the ingredients indicated in Table 3 below:

TABLE 3

Formulation of diffusion layer 2

| No. | Starting material | per dose mg |
|---|---|---|
| 1 | Active ingredient pellets with diffusion layer 1 (as in Table 2) | 166.510 |
| 2 | Polyvinyl acetate stabilized with polyvinylpyrrolidone and sodium lauryl sulphate (Kollicoat SR 30 D) | 9.000 |
| 3 | Polyvinyl alcohol-polyethylene glycol copolymer (Kollicoat IR) | 0.405 |
| 4 | Propylene glycol | 0.900 |
| 5 | Talc | 0.360 |
| | Total amount per dose | 177.175 |

The active ingredient pellets provided with the active ingredient and diffusion layer 1 and obtained using the ingredients in Table 2 are sprayed with an aqueous suspension of polyvinyl acetate as matrix material and polyvinyl alcohol-polyethylene glycol copolymer as pore former, propylene glycol as plasticizer and talc as antitack agent. As is evident, the material for forming diffusion layer 2 comprises a smaller amount of the pore former polyvinyl alcohol-polyethylene glycol copolymer and accordingly leads to a diffusion layer with a lower permeability for the diffusing active ingredient (1R,3r,5S)-3-[(hydroxydiphenylacetyl)oxy]-spiro[8-azoniabicyclo[3.2.1]octane-8,1'-pyrrolidinium]chloride.

The active ingredient carriers provided with the two diffusion layers in this way are subsequently provided with a gastro-resistant coating using the formulation indicated in Table 4 below:

TABLE 4

Formulation, application of a gastro-resistant coating

| No. | Starting material | per dose mg |
|---|---|---|
| 1 | Active ingredient pellets with diffusion layers 1 and 2 (as in Table 3) one dose comprises 45 mg of active ingredient | 177.175 |
| 2 | Methacrylic acid-ethyl acrylate copolymer (Kollicoat MAE 30 DP) | 28.000 |
| 3 | Talc | 12.600 |
| 4 | Propylene glycol | 4.200 |
| 5 | Sodium carboxymethylcellulose (Tylopur C30 GI) | 0.720 |
| | Total amount per dose | 222.695 |

The active ingredient pellets obtained with both diffusion layers 1 and 2 are then provided with the gastro-resistant coating layer using the formulation indicated in Table 4 above, with an aqueous suspension of methacrylic acid-ethyl acrylate copolymer as matrix material, propylene glycol as plasticizer, sodium carboxymethylcellulose as binder and talc as antitack agent being continuously sprayed onto the active ingredient pellets provided with both diffusion layers 1 and 2 and simultaneously dried at an inlet air temperature of 35 to 80° C., resulting in the pharmaceutical preparation of the invention in the form of the active ingredient pellets provided with the active ingredient.

EXAMPLE 2

(Comparative) Batch: 050047

For comparison, active ingredient carriers provided with active ingredient using the same ingredients and the same ratios of amounts but comprising the ingredients of diffusion layers 1 and 2 of the invention not in separate layers but in a single diffusion layer are produced.

For this purpose, active ingredient carriers provided with the active ingredient (1R,3r,5S)-3-[(hydroxy-diphenylacetyl)oxy]spiro[8-azoniabicyclo[3.2.1]octane-8,1'-pyrrolidinium]chloride using the ingredients indicated in Table 1 of Example 1 are produced and provided with a diffusion layer using the ingredients listed in Table 5 below:

TABLE 5

Formulation of diffusion layer 1 + 2 applied as mixture

| No. | Starting material | per dose mg |
|---|---|---|
| 1 | Active ingredient pellets (as in Table 1) | 154.450 |
| 2 | Polyvinyl acetate stabilized with polyvinylpyrrolidone and sodium lauryl sulphate (Kollicoat SR 30 D) | 18.000 |
| 3 | Polyvinyl alcohol-polyethylene glycol copolymer (Kollicoat IR) | 2.205 |
| 4 | Propylene glycol | 1.800 |
| 5 | Talc | 0.720 |
|   | Total amount per dose | 177.175 |

A gastro-resistant coating is then applied by the procedure of Example 1, and using the ingredients indicated in Table 4 of Example 1, to the active ingredient pellets provided with diffusion layer 1+2, applied as mixture, obtained in this way, and active ingredient pellets of the composition indicated in Table 6 below are obtained:

TABLE 6

| No. | Starting material | per dose mg |
|---|---|---|
| 1 | Active ingredient pellets with diffusion layer 1 + 2 (as in Table 5) one dose comprises 45 mg of active ingredient | 177.175 |
| 2 | Methacrylic acid-ethyl acrylate copolymer (Kollicoat MAE 30 DP) | 28.000 |
| 3 | Talc | 12.600 |
| 4 | Propylene glycol | 4.200 |
| 5 | Sodium carboxymethylcellulose (Tylopur C30 G1) | 0.720 |
|   | Total amount per dose | 222.695 |

EXAMPLE 3

(Comparative) Batch: 050046/1

As further comparative example, active ingredient carriers provided only with the active ingredient (1R,3r,5S)-3-[(hydroxydiphenylacetyl)oxy]spiro[8-azoniabicyclo[3.2.1]octane-8,1'-pyrrolidinium]chloride and not comprising either a diffusion layer or a gastro-resistant coating are prepared, specifically by the procedure of Example 1 and using the ingredients indicated in Table 1, resulting in the active ingredient carriers provided with the active ingredient (1R,3r,5S)-3-[(hydroxydiphenylacetyl)oxy]spiro[8-azoniabicyclo[3.2.1]octane-8,1'-pyrrolidinium]chloride) of the composition indicated in Table 7 below.

TABLE 7

| No. | Starting material | per dose mg |
|---|---|---|
| 1 | Active ingredient | 45.000 |
| 2 | Neutral pellets | 100.000 |
| 3 | Hydroxypropylmethylcellulose [hypromellose] | 4.5000 |
| 4 | Talc | 4.5000 |
| 5 | Polyethylene glycol 6000 (macrogol 6000) | 0.450 |
|   | Total amount per dose | 154.450 |

EXAMPLE 4

(Comparative) Batch: 050048

This comparative example relates to active ingredient carriers provided with the active ingredient (1R,3r,5S)-3-[(hydroxydiphenylacetyl)oxy]spiro[8-azoniabicyclo[3.2.1]octane-8,1'-pyrrolidinium]chloride and provided only with one diffusion layer, specifically diffusion layer 1 of Example 1 of the present invention, and the gastro-resistant coating layer.

The starting material comprises the active ingredient pellets provided with the active ingredient which had been obtained by the procedure of Example 1 using the ingredients indicated in Table 1.

These active ingredient carriers are provided only with diffusion layer 1 using the ingredients and the procedure indicated for forming diffusion layer 1 in Example 1 with reference to Table 2.

Application of a gastro-resistant coating layer by the procedure of Example 1 using the ingredients indicated in Table 4 results in active ingredient pellets loaded with the active ingredient of the composition indicated in Table 8 below:

TABLE 8

| No. | Starting material | per dose mg |
|---|---|---|
| 1 | Active ingredient pellets with diffusion layer 1 one dose comprises 45 mg of active ingredient | 166.510 |
| 2 | Methacrylic acid-ethyl acrylate copolymer (Kollicoat MAE 30 DP) | 28.000 |
| 3 | Talc | 12.600 |
| 4 | Propylene glycol | 4.200 |
| 5 | Sodium carboxymethylcellulose (Tylopur C30 G1) | 0.720 |
|   | Total amount per dose | 212.030 |

EXAMPLE 5

(Comparative) Batch: 050049

This comparative example relates to active ingredient carriers provided with the active ingredient (1R,3r,5S)-3-[(hydroxydiphenylacetyl)oxy]spiro[8-azoniabicyclo[3.2.1]octane-8,1'-pyrrolidinium]chloride and provided only with diffusion layer 2 of the pharmaceutical preparation of the invention according to Example 1 and with the gastro-resistant coating layer.

The starting material for this purpose comprises the active ingredient carriers provided with the active ingredient which had been produced using the ingredients indicated in Table 1 of Example 1 by the procedure described therein.

Diffusion layer 2 is applied to these active ingredient pellets provided with the active ingredient, using the ingredients indicated in Table 9 below and employing the procedure indicated in connection with Table 3 in Example 1.

TABLE 9

| No. | Starting material | per dose mg |
|---|---|---|
| 1 | Active ingredient pellets (as in Table 1) | 154.450 |
| 2 | Polyvinyl acetate stabilized with polyvinylpyrrolidone and sodium lauryl sulphate (Kollicoat SR 30D) | 9.000 |
| 3 | Polyvinyl alcohol-polyethylene glycol copolymer (Kollicoat IR) | 0.405 |
| 4 | Propylene glycol | 0.900 |
| 5 | Talc | 0.360 |
|   | Total amount per dose | 165.115 |

Application of a gastro-resistant coating layer by the procedure of Example 1 using the ingredients indicated in Table 4 results in active ingredient pellets with diffusion layer 2 and the composition indicated in Table 10 below.

TABLE 10

Formulation, application of a gastro-resistant coating

| No. | Starting material | per dose mg |
|---|---|---|
| 1 | Active ingredient pellets with diffusion layer 2 one dose comprises 45 mg of active ingredient | 165.115 |
| 2 | Methacrylic acid-ethyl acrylate copolymer (Kollicoat MAE 30 DP) | 28.000 |
| 3 | Talc | 12.600 |
| 4 | Propylene glycol | 4.200 |
| 5 | Sodium carboxymethylcellulose (Tylopur C30 G1) | 0.720 |
|   | Total amount per dose | 210.635 |

EXAMPLE 6

Investigation of the In Vitro Release of the Active Ingredient (1R,3r,5S)-3-[(hydroxydiphenylacetyl)oxy]-spiro[8-azoniabicyclo[3.2.1]octane-8,1'-pyrrolidinium]Chloride from the Active Ingredient Pellets obtained as in Examples 1 to 5 Above To investigate the release of active ingredient as a function of time, the US Pharmacopeia method for determining the release of products with a gastro-resistant coating No. 724 Method A is employed as follows:

Acid Stage

| Apparatus: | paddle stirrer |
|---|---|
| Speed of rotation: | 200 min$^{-1}$ |
| Temperature: | 37 ± 0.5° C. |
| Dissolving medium: | 750 ml of 0.1 M hydrochloric acid |

A dose of active ingredient pellets produced according to the above examples is introduced into the apparatus, the vessel is covered and the paddle stirrer is operated for 2 hours. A sample is then taken to determine the active ingredient (1R, 3r,5S)-3-[(hydroxydiphenylacetyl)oxy]spiro[8-azoniabicyclo-[3.2.1]octane-8,1'-pyrrolidinium]chloride.

Buffer Stage 250 ml of a 0.20 M tribasic sodium phosphate solution equilibrated at 37±0.5° C. are added to the acid stage (750 ml of 0.1M hydrochloric acid). The pH is adjusted to a value of 6.8±0.05 if necessary with 2 N hydrochloric acid or 2 N sodium hydroxide solution. The apparatus is, operated for 2 hours and then samples are taken after 15, 30, 45, 60, 75, 90, 105 and 120 minutes, and the active ingredient therein is determined by HPLC.

Reference Solution:

0.045 mg/ml (1R,3r,5S)-3-[(hydroxydiphenylacetyl)oxy]-spiro[8-azoniabicyclo[3.2.1]octane-8,1'-pyrrolidinium] chloride RS in 0.1 N hydrochloric acid.

HPLC Chromatography Conditions

The chromatography takes place using:

a column of stainless steel with a length of 0.125 m and an internal diameter of 4 mm, which is packed with octadecylsilyl gel for chromatographic purposes (5 μm), specifically Nucleosil 100-5 C18;

a mixture of 65 volumes of purified water which comprises 2.202 g/l sodium heptane sulphonate and 0.4 ml/l triethylamine and has been adjusted to a pH of 2.5 with concentrated phosphoric acid, and 35 volumes of acetonitrile, is used as mobile phase.

A speectrophotometer (DAD 210.10, 400.100 nm); set at 210 nm is used as detector;

the temperature of the column is kept at 40° C.

25 μl of the sample liquid are injected, and the chromatography is performed for about 4.5 minutes.

The concentration of dissolved (1R,3r,5S)-3-[(hydroxy-diphenylacetyl)oxy]spiro[8-azoniabicyclo[3.2.1]octane-8, 1'-pyrrolidinium]chloride is calculated in percent using the following equation:

$$Y = CR_{(w)} \cdot AT_{(w)} \cdot 100 / AR_{(w)} \cdot CT_{(w)}$$

in which

Y: dissolved active ingredient (1R,3r,5S)-3-[(hydroxydiphenylacetyl)oxy]spiro[8-azoniabicyclo[3.2.1]octane-8,1'-pyrrolidinium]chloride (% of the stated content)

$CT_{(w)}$: nominal concentration of active ingredient in the test solution (0.045 mg/ml)

$CR_{(w)}$: concentration of the active ingredient in the reference solution $AT_{(w)}$: area of active ingredient peak of the test solution $AR_{(w)}$: area of reference substance peak in the reference solution The results of the release of active ingredient obtained in this investigation of the active ingredient pellets of Examples 1 to 5 are compiled in Table 11 below:

PU040014 W 45 Tablets MOF

Active Ingredient Pellets and Gastro-Resistant Pellets Differing in Application of the Diffusion Layers

TABLE 11

Results of the release of active ingredient*

|  | Ex. 3 (Ref.) | Ex. 1 (invention) | Ex. 2 (comp.) | Ex. 4 (comp.) | Ex. 5 (comp.) |
|---|---|---|---|---|---|
| Test time Batch | Active ingredient pellets without diffusion layer 050046/1 | Diffusion layer 1 + 2 applied successively 050046/2 | Diffusion layer 1 + 2 applied as mixture 050047 | Diffusion layer 1 applied alone 050048 | Diffusion layer 2 applied alone 050049 |
| 0 | 0.00 | 0 | 0 | 0 | 0 |
| 15 | 98.02 | 0.76 | 73.94 | 101.02 | 7.02 |
| 30 | 98.30 | 8.14 | 91.12 | 101.24 | 34.27 |

TABLE 11-continued

| | Results of the release of active ingredient* | | | | |
|---|---|---|---|---|---|
| | Ex. 3 (Ref.) | Ex. 1 (invention) | Ex. 2 (comp.) | Ex. 4 (comp.) | Ex. 5 (comp.) |
| | | | Test time | | |
| Batch | Active ingredient pellets without diffusion layer 050046/1 | Diffusion layer 1 + 2 applied successively 050046/2 | Diffusion layer 1 + 2 applied as mixture 050047 | Diffusion layer 1 applied alone 050048 | Diffusion layer 2 applied alone 050049 |
| 45 | 98.39 | 29.89 | 97.84 | 101.03 | 67.08 |
| 60 | 98.47 | 51.13 | 98.75 | 101.20 | 81.80 |
| 75 | 98.65 | 65.47 | 99.59 | 101.25 | 88.84 |
| 90 | 98.56 | 74.35 | 99.45 | 101.30 | 92.39 |
| 105 | 98.49 | 80.03 | 99.99 | 101.35 | 94.63 |
| 120 | 98.68 | 84.09 | 99.89 | 101.10 | 95.87 |

*(1R,3r,5S)-3-[(hydroxydiphenylacetyl)oxy]spiro[8-azo-niabicyclo[3.2.1]octane-8,1'-pyrrolidinium] chloride The results of Table 11 above are depicted as a graph in FIG. 1 below, specifically by plotting the percentage release of active ingredient as a function of time.

As is evident from FIG. 1 above, the pharmaceutical preparation (050046/2) of the invention shows the best course as desired according to the invention for the release of active ingredient in vitro with a slow rise and subsequent almost constant release of active ingredient, whereas the comparative products having no diffusion layer (050046/1) or having in each case only one diffusion layer 1 or 2 (050049 and 050048) or the active ingredient pellets of Example 2 in which the ingredients of the two diffusion layers 1 and 2 of the invention are present in a single diffusion layer (050047) show a fast rise in the curves and thus an unwanted rapid release of active ingredient.

It is to be regarded as surprising that the pharmaceutical preparation of the invention in which the inner layer is formed from at least two diffusion layers whose permeability for the diffusing active ingredient decreases from the inside to the outside shows a considerably better course of release of active ingredient than the active ingredient pellets of Example 2, in which the same ingredients for forming the two diffusion layers of the invention are present in a single diffusion layer. This pharmaceutical preparation also shows an unwantedly rapid release of active ingredient at the start, since approximately 95% are released after only 40 minutes, at a time when the pharmaceutical preparation of the invention results in a release of only about 20% active ingredient.

It is thus possible with the pharmaceutical preparation of the invention to achieve, by comparison with a single administration of a pharmaceutical product rapidly releasing the active ingredient (1R,3r,5S)-3-[(hydroxydiphenylacetyl) oxy]spiro[8-azoniabicyclo-[3.2.1]octane-8,1'-pyrrolidinium]chloride, a slower rise in the level of active ingredient in the plasma with an overall lower blood level, and thus to overcome the disadvantages of conventional products of this type.

The invention claimed is:

1. A pharmaceutical preparation for oral administration with controlled release of active ingredient in the small bowel comprising:
   a) active ingredient carriers comprising (1R,3r,5S)-3-[(hydroxydiphenylacetyl)oxy]spiro[8-azoniabicyclo[3.2.1] octane-8,1'-pyrrolidinium]chloride as the active agent, and optionally a binder, buffer substances, a plasticizer and/or an antitack agent;
   b) an inner layer coated on the active ingredient carriers to control the release of active ingredient comprising:
      i) a first diffusion layer comprising polyvinyl acetate as the matrix material and polyvinyl alcohol-polyethylene glycol copolymers as the pore former, and optionally a plasticizer and/or an antitack agent; and
      ii) a second diffusion layer comprising polyvinyl acetate as the matrix material and polyvinyl alcohol-polyethylene glycol copolymers as the pore former present in an amount less than the amount of pore former used in the first diffusion layer, and optionally a plasticizer and/or an antitack agent; and
   c) optionally, a gastro-resistant coating layer disposed thereon,
   wherein the permeability for the diffusing active ingredient decreases from the inside to the outside; and
   wherein <75% of the active agent of the pharmaceutical preparation is released in 60 minutes releasing the active agent at a constant rate.

* * * * *